(12) United States Patent
Komiya (10) Patent No.: US 8,036,438 B2
(45) Date of Patent: Oct. 11, 2011

(54) OUTLINE DETECTION APPARATUS, OUTLINE DETECTION METHOD, AND PROGRAM THEREOF

(75) Inventor: Yasuhiro Komiya, Tokyo (JP)

(73) Assignee: Olympus Corporation, Tokyo (JP)

( * ) Notice: Subject to any disclaimer, the term of this patent is extended or adjusted under 35 U.S.C. 154(b) by 877 days.

(21) Appl. No.: 12/075,781

(22) Filed: Mar. 12, 2008

(65) Prior Publication Data

US 2008/0232662 A1    Sep. 25, 2008

(30) Foreign Application Priority Data

Mar. 16, 2007   (JP) .............................. P2007-069227

(51) Int. Cl.
*G06K 9/00* (2006.01)
(52) U.S. Cl. ....................................... 382/128; 382/100
(58) Field of Classification Search ................. 382/128, 382/100, 162; 348/66; 356/419; 433/26
See application file for complete search history.

(56) References Cited

U.S. PATENT DOCUMENTS

| | | | |
|---|---|---|---|
| 5,717,605 A | 2/1998 | Komiya et al. | |
| 6,007,332 A * | 12/1999 | O'Brien | 433/26 |
| 7,574,025 B2 * | 8/2009 | Feldman | 382/128 |
| 7,785,103 B2 * | 8/2010 | Jung et al. | 433/29 |
| 2007/0036430 A1 | 2/2007 | Katsumata et al. | |
| 2007/0140553 A1 * | 6/2007 | Katsumata | 382/162 |
| 2008/0292154 A1 * | 11/2008 | Nishimura et al. | 382/128 |

FOREIGN PATENT DOCUMENTS

| | | |
|---|---|---|
| EP | 1 842 481 A1 | 10/2007 |
| JP | 7-120324 A | 5/1995 |
| JP | 09-043058 A | 2/1997 |
| JP | 2000-185060 A | 7/2000 |
| JP | 2001-188905 A | 7/2001 |
| JP | 2006-166990 A | 6/2006 |
| JP | 2006-202135 A | 8/2006 |
| JP | 2007-047045 A | 2/2007 |

* cited by examiner

*Primary Examiner* — Stephen Koziol
(74) *Attorney, Agent, or Firm* — Holtz, Holtz, Goodman & Chick, PC (57) ABSTRACT

An outline detection apparatus which detects an outline of a tooth in a dental image, including: a rectangular range specification device for estimating portions in the dental image as a tooth, gum, and background respectively, and specifying rectangular ranges with predetermined pixels in the positions estimated as the tooth, gum, and background; and a site estimation device for acquiring a characteristic quantity based on color information of the pixels in the rectangular ranges, finding a classification vector which maximizes the Fischer ratio based on the characteristic quantity, and estimating which of the tooth range, the gum range, and the background range, pixels other than the pixels in the rectangular ranges are positioned in according to comparison between a predetermined threshold value and an inner product between the classification vector and a pixel value vector based on color information on pixels other than the pixels in the rectangular ranges.

17 Claims, 7 Drawing Sheets

OUTLINE DETECTION APPARATUS, OUTLINE DETECTION METHOD, AND PROGRAM THEREOF

BACKGROUND OF THE INVENTION

1. Field of the Invention

The present invention relates to an outline detection apparatus, an outline detection method, and a program thereof.

Priority is claimed on Japanese Patent Application No. 2007-069227, filed on Mar. 16, 2007, the content of which is incorporated herein by reference.

2. Description of Related Art

In the field of dentistry, medical treatments by the ceramic crown method and the like are performed. In this ceramic crown method, a crown (a prosthetic crown made of ceramics) with a color similar to that of the original tooth of a patient is fabricated, and then is placed on the tooth of the patient. In the medical treatment by the ceramic crown method, fabrication of a crown as a prosthesis is indispensable.

Here, to fabricate a crown, an application software for taking an image of a tooth of a patient to allow a dentist or a dental technician to correctly examine the color and shape of the tooth is required.

In such an application, a technology for correctly detecting the outline of a tooth is required. As a technology relevant to the present invention, there is disclosed a technology for detecting a boundary of a surface of biological mucosae in an image taken by an endoscope to detect the presence of biological mucosae with different descriptions. (see Japanese Unexamined Patent Application, First Publication No. 2006-166990)

SUMMARY OF THE INVENTION

The present invention is an outline detection apparatus which detects at least an outline of a tooth in a dental image of which are taken at least the tooth, a gum, and a background showing an inside of a mouth other than the tooth and the gum, including: a rectangular range specification device for estimating a central portion of the dental image as a tooth, estimating a position in a predetermined range in an upper or lower portion of the dental image as a gum according to a specification of a dental image on a maxillary area or a mandibular area, estimating a position in a predetermined range in the lower portion as the background if the position estimated as the gum is in the upper portion of the dental image, or estimating a position in a predetermined range in the upper portion as the background if the position estimated as the gum is in the lower portion of the dental image, and specifying rectangular ranges with predetermined pixels in a part of the positions estimated as the tooth, the gum, and the background; and a site estimation device for acquiring from data on the dental image a characteristic quantity based on color information of the respective pixels in the rectangular ranges, finding a classification vector which maximizes the Fischer ratio based on the acquired characteristic quantity, and estimating which of the tooth range, the gum range, and the background range, pixels in the dental image other than the respective pixels in the rectangular ranges are positioned in according to comparison between a predetermined threshold value and an inner product between the classification vector and a pixel value vector based on color information on pixels in the dental image other than the respective pixels in the rectangular ranges.

Furthermore, in the outline detection apparatus of the present invention, it is preferable that the site estimation device separately perform: processing in which the rectangular range in a part of the position estimated as the tooth and the rectangular range in a part of the position estimated as the gum are used to estimate a boundary between a tooth and a gum according to which of the tooth range and the gum range, the pixels in the dental image other than the respective pixels within the rectangular ranges are positioned in; and processing in which the rectangular range in a part of the position estimated as the tooth and the rectangular range in a part of the position estimated as the background are used to estimate a boundary between a tooth and a background according to which of the tooth range and the background range, the pixels in the dental image other than the respective pixels within the rectangular ranges are positioned in.

Furthermore, in the outline detection apparatus of the present invention, it is preferable that when estimating a boundary between a tooth and a gum by use of the rectangular range in a part of the position estimated as the tooth and the rectangular range in a part of the position estimated as the gum, the site estimation device use a new rectangular range, which is the rectangular range in a part of the position estimated as the tooth-moved toward the gum, and a new rectangular range, which is the rectangular range in a part of the position estimated as the gum moved toward the tooth, to repeat processing for estimating a boundary between a tooth and a gum according to which of the tooth range and the gum range, the pixels in the dental image other than the respective pixels within the rectangular ranges are positioned in, the processing being repeated the same number of times as the new rectangular range, which is the rectangular range in a part of the position estimated as the tooth moved toward the gum, and the new rectangular range, which is the rectangular range in a part of the position estimated as the gum moved toward the tooth, are gradually brought closer to each other.

Furthermore, in the outline detection apparatus of the present invention, it is preferable that when estimating a boundary between a tooth and a background by use of the rectangular range in a part of the position estimated as the tooth and the rectangular range in a part of the position estimated as the background, the site estimation device use a new rectangular range, which is the rectangular range in a part of the position estimated as the tooth moved toward the background, and a new rectangular range, which is the rectangular range in a part of the position estimated as the background moved toward the tooth, to repeat processing for estimating a boundary between a tooth and a background according to which of the tooth range and the background range, the pixels in the dental image other than the respective pixels within the rectangular ranges are positioned in, the processing being repeated the same number of times as the new rectangular range, which is the rectangular range in a part of the position estimated as the tooth moved toward the background, and the new rectangular range, which is the rectangular range in a part of the position estimated as the background moved toward the tooth, are gradually brought closer to each other.

Furthermore, it is preferable that the outline detection apparatus of the present invention further include an outline calculation portion which determines whether or not a pixel is the pixel estimated as in the tooth range one by one from the pixel in the vicinity of the tooth toward the rectangular range in a part of the position estimated as the tooth, and then identifies, one by one from a pixel initially estimated as in the tooth range, a boundary pixel that is another pixel estimated as in the tooth range and is in contact with the pixel estimated as in a site other than the tooth, to thereby determine a set of the boundary pixels as an outline.

Furthermore, in the outline detection apparatus of the present invention, it is preferable that the site estimation device specify the rectangular range or the new rectangular range in a part of the position estimated as the tooth outside a region of the tooth in which light is specularly reflected.

Furthermore, the present invention is an outline detection method which detects at least an outline of a tooth in a dental image of which are taken at least the tooth, a gum, and a background showing an inside of a mouth other than the tooth and the gum, including: a rectangular range specification process for estimating a central portion of the dental image as a tooth, estimating a position in a predetermined range in an upper or lower portion of the dental image as a gum according to a specification of a dental image on a maxillary area or a mandibular area, estimating a position in a predetermined range in the lower portion as the background if the position estimated as the gum is in the upper portion of the dental image, or estimating a position in a predetermined range in the upper portion as the background if the position estimated as the gum is in the lower portion of the dental image, and specifying rectangular ranges with predetermined pixels in a part of the positions estimated as the tooth, the gum, and the background; and a site estimation process for acquiring from data on the dental image a characteristic quantity based on color information of the respective pixels in the rectangular ranges, finding a classification vector which maximizes the Fischer ratio based on the acquired characteristic quantity, and estimating which of the tooth range, the gum range, and the background range, pixels in the dental image other than the respective pixels in the rectangular ranges are positioned in according to comparison between a predetermined threshold value and an inner product between the classification vector and a pixel value vector based on color information on pixels in the dental image other than the respective pixels in the rectangular ranges.

Furthermore, in the outline detection method of the present invention, it is preferable that the site estimation process include a process for separately performing: processing in which the rectangular range in a part of the position estimated as the tooth and the rectangular range in a part of the position estimated as the gum are used to estimate a boundary between a tooth and a gum according to which of the tooth range and the gum range, the pixels in the dental image other than the respective pixels within the rectangular ranges are positioned in; and processing in which the rectangular range in a part of the position estimated as the tooth and the rectangular range in a part of the position estimated as the background are used to estimate a boundary between a tooth and a background according to which of the tooth range and the background range, the pixels in the dental image other than the respective pixels within the rectangular ranges are positioned in.

Furthermore, in the outline detection method of the present invention, it is preferable that the site estimation process include a process in which when estimating a boundary between a tooth and a gum by use of the rectangular range in a part of the position estimated as the tooth and the rectangular range in a part of the position estimated as the gum, the site estimation process uses a new rectangular range, which is the rectangular range in a part of the position estimated as the tooth moved toward the gum, and a new rectangular range, which is the rectangular range in a part of the position estimated as the gum moved toward the tooth, to repeat processing for estimating a boundary between a tooth and a gum according to which of the tooth range and the gum range, the pixels in the dental image other than the respective pixels within the rectangular ranges are positioned in, the site estimation device of the outline detection apparatus repeating the processing the same number of times as the new rectangular range, which is the rectangular range in a part of the position estimated as the tooth moved toward the gum, and the new rectangular range, which is the rectangular range in a part of the position estimated as the gum moved toward the tooth, are gradually brought closer to each other.

Furthermore, in the outline detection method of the present invention, it is preferable that the site estimation process include a process in which when estimating a boundary between a tooth and a background by use of the rectangular range in a part of the position estimated as the tooth and the rectangular range in a part of the position estimated as the background, the site estimation process uses a new rectangular range, which is the rectangular range in a part of the position estimated as the tooth moved toward the background, and a new rectangular range, which is the rectangular range in a part of the position estimated as the background moved toward the tooth, to repeat processing for estimating a boundary between a tooth and a background according to which of the tooth range and the background range, the pixels in the dental image other than the respective pixels within the rectangular ranges are positioned in, the site estimation device of the outline detection apparatus repeating the processing the same number of times as the new rectangular range, which is the rectangular range in a part of the position estimated as the tooth moved toward the background, and the new rectangular range, which is the rectangular range in a part of the position estimated as the background moved toward the tooth, are gradually brought closer to each other.

Furthermore, it is preferable that the outline detection method of the present invention further include an outline calculation process which determines whether or not a pixel is the pixel estimated as in the tooth range one by one from the pixel in the vicinity of the tooth toward the rectangular range in a part of the position estimated as the tooth, and then identifies, one by one from a pixel initially estimated as in the tooth range, a boundary pixel that is another pixel estimated as in the tooth range and is in contact with the pixel estimated as in a site other than the tooth, to thereby determine a set of the boundary pixels as an outline.

Furthermore, it is preferable that the outline detection method of the present invention include a process for specifying the rectangular range or the new rectangular range in a part of the position estimated as the tooth outside a region of the tooth in which light is specularly reflected.

Furthermore, the present invention is a program of allowing a computer of an outline detection apparatus which detects at least an outline of a tooth of a dental image of which are taken at least the tooth, a gum, and a background showing an inside of a mouth other than the tooth and the gum to execute: rectangular range specification processing for estimating a central portion of the dental image as a tooth, estimating a position in a predetermined range in an upper or lower portion of the dental image as a gum according to a specification of a dental image on a maxillary area or a mandibular area, estimating a position in a predetermined range in the lower portion as the background if the position estimated as the gum is in the upper portion of the dental image, or estimating a position in a predetermined range in the upper portion as the background if the position estimated as the gum is in the lower portion of the dental image, and specifying rectangular ranges with predetermined pixels in a part of the positions estimated as the tooth, the gum, and the background; and site estimation processing for acquiring from data on the dental image a characteristic quantity based on color information of the respective pixels in the rectangular ranges, finding a classification vector which maximizes the Fischer ratio based on the acquired characteristic quantity, and estimating which of the tooth range, the gum range, and the background range, pixels in the dental image other than the respective pixels in the rectangular ranges are positioned in according to comparison between a predetermined threshold value and an inner product between the classification vector and a pixel value vector based on color information on pixels in the dental image other than the respective pixels in the rectangular ranges.

DETAILED DESCRIPTION OF THE INVENTION

Figure 1:
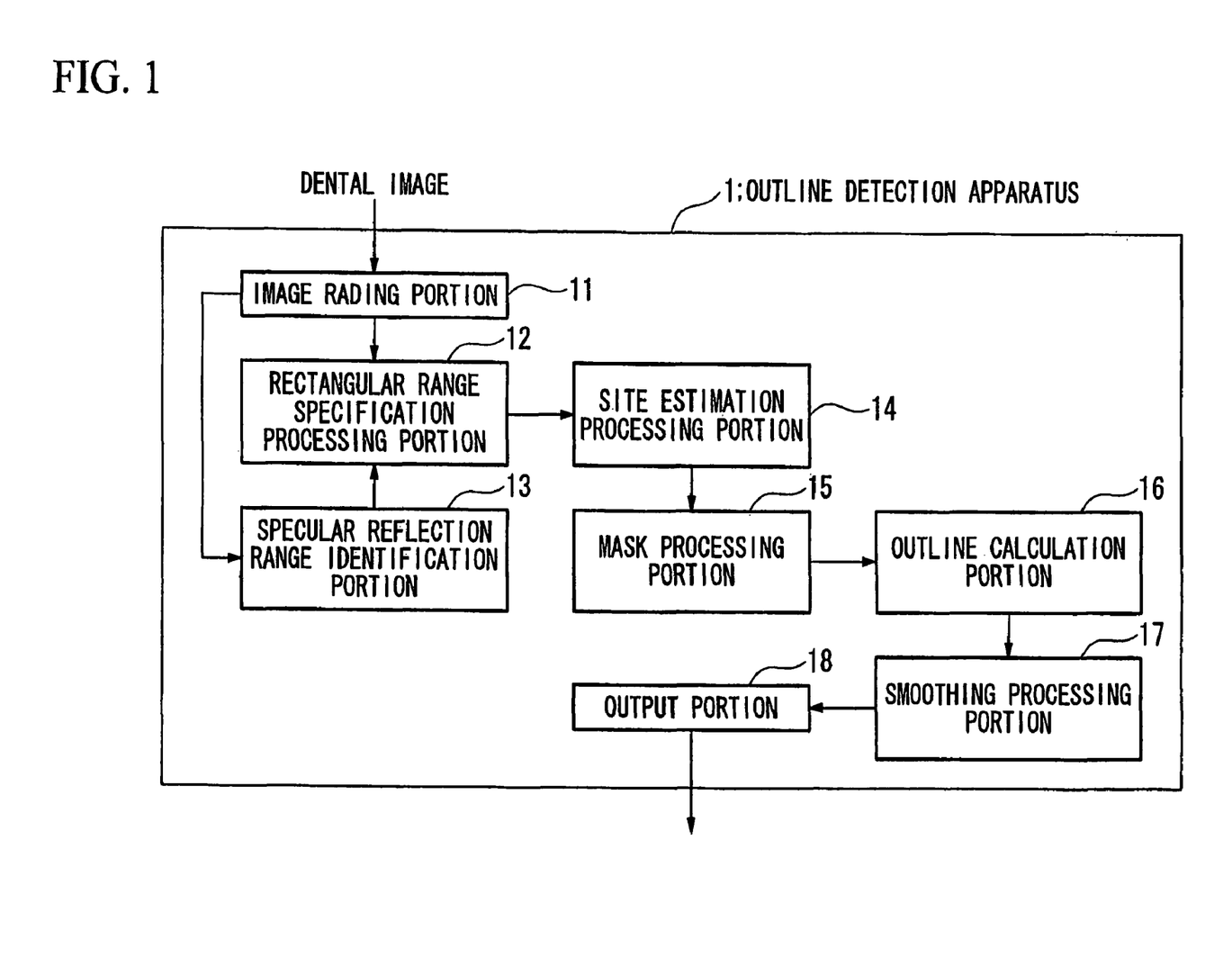
FIG. 1 is a block diagram showing a configuration of an outline detection apparatus.

Hereunder is a description of an outline detection apparatus according to one embodiment of the present invention with reference to the drawings. FIG. 1 is a block diagram showing a configuration of the outline detection apparatus according to the embodiment. In this figure, reference numeral 1 denotes an outline detection apparatus. The outline detection apparatus 1 has: an image reading portion 11 for reading data on a dental image of which a tooth, a gum, and a background showing an inside of a mouth other than the tooth and the gum are taken; a rectangular range specification processing portion 12 for specifying a rectangular range with a predetermined number of pixels in a portion of a position estimated as a tooth, a gum, and a background; a specular reflection region identification portion 13 for identifying pixels included in a region in which light of a tooth in the dental image is specularly reflected; a site estimation processing portion 14 for estimating to which portion of the tooth, the gum, and the background, the respective pixels in the dental image correspond; a mask processing portion 15 for correcting a range which although corresponding to a gum site in terms of position, is erroneously recognized as in a range of a tooth into a range of a gum; an outline calculation portion 16 for calculating an outline of a tooth; a smoothing processing portion 17 for separating adjacent teeth and correcting an outline into a smooth line; and an output portion 18 for outputting a dental image in which an outline is displayed.

First, the rectangular range specification processing portion 12 estimates a central portion of the dental image as a tooth, estimates a position in a predetermined range in an upper or lower portion of the dental image as a gum according to a specification of a dental image on a maxillary area or a mandibular area, estimates a position in a predetermined range in the lower portion as the background if the position estimated as the gum is in the upper portion of the dental image, or estimates a position in a predetermined range in the upper portion as the background if the position estimated as the gum is in the lower portion of the dental image, and specifies rectangular ranges with predetermined pixels in a part of the positions estimated as the tooth, the gum, and the background. Note that the rectangular range specification processing portion 12 specifies the rectangular range outside the area which the specular reflection region identification portion 13 has identified as a region in a tooth in which light is specularly reflected. The site estimation processing portion 14 acquires from data on the dental image a characteristic quantity based on color information of the respective pixels in the rectangular ranges, finds a classification vector which maximizes the Fischer ratio based on the acquired characteristic quantity, and estimates which of the tooth range, the gum range, and the background range, pixels in the dental image other than the respective pixels in the rectangular ranges are positioned in according to comparison between a predetermined threshold value and an inner product between the classification vector and a pixel value vector based on color information on pixels in the dental image other than the respective pixels in the rectangular ranges. An outline of the tooth is corrected through processing by the mask processing portion 15, the outline calculation portion 16, and the smoothing processing portion 17, and a dental image where the outline is displayed is output by the output portion 18. As a result, detection accuracy of an outline of a tooth in a dental image can be increased.

Figure 2:
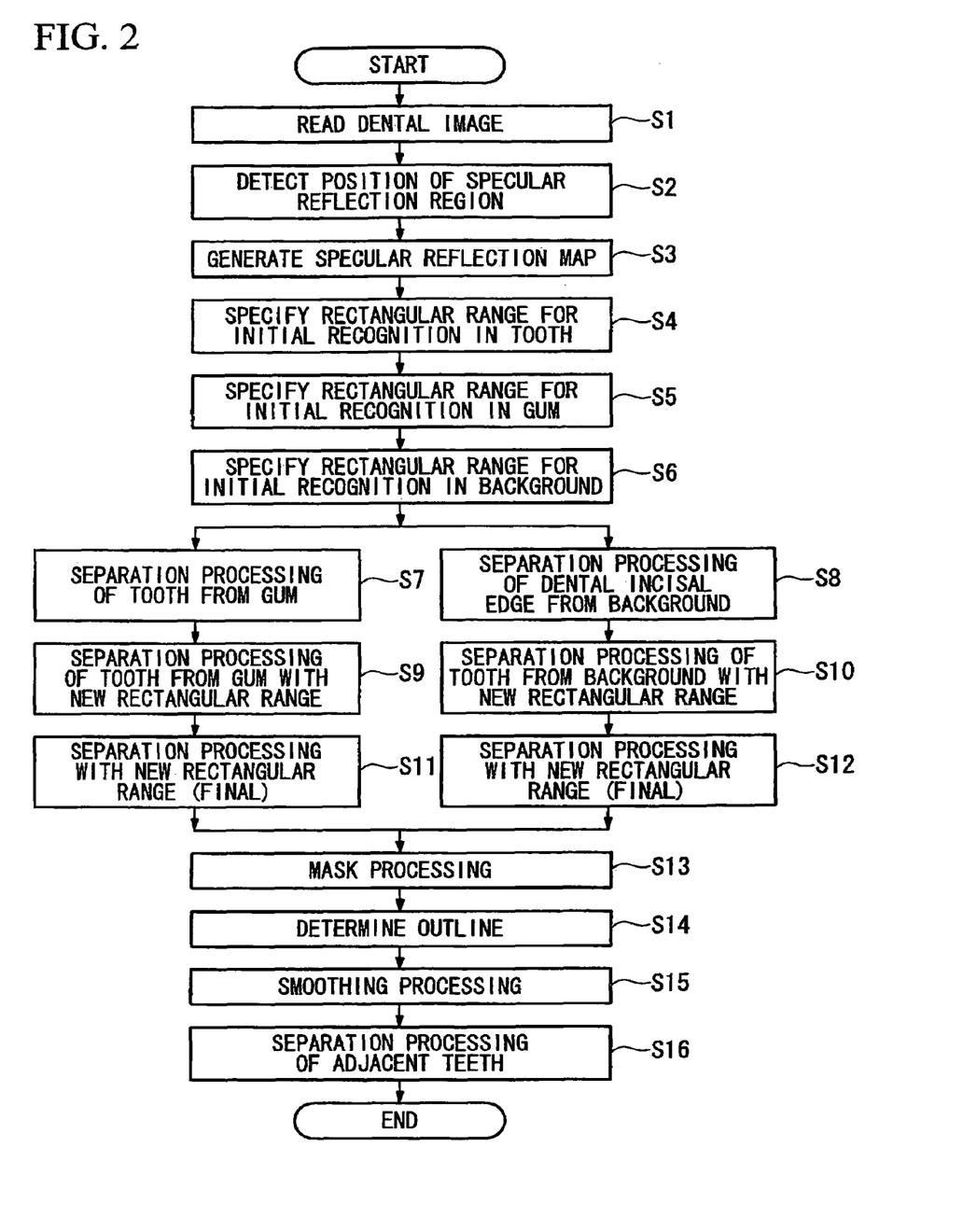
FIG. 2 shows a processing flow of an outline detection apparatus.

FIG. 2 shows a processing flow of the outline detection apparatus.

Next is a detailed, sequential description of processing by the outline detection apparatus 1.

First, the image reading portion 11 reads a dental image (step S1). This dental image is taken by a dental image taking apparatus, of which at least a tooth, a gum, a background showing an inside of a mouth other than the tooth and the gum are taken. The dental image holds information with respect to R (Red), G (Green), B (Blue), luminance, etc. as information on the respective pixels. It is assumed that the dental image taking apparatus has sequentially irradiated illumination light in seven types of wavelength bands (illumination light in seven colors; seven bands) onto a photographic subject (a tooth of a patient) to capture seven spectral images of the photographic subject as still images (multiband imaging), and hence information on these seven spectral images of the photographic subject is stored in the respective pixels of the dental image. After reading a dental image, the image reading portion 11 transfers the dental image to the rectangular range specification processing portion 12 and the specular reflection region identification portion 13. In the present embodiment, data of one dental image stores data on the seven spectral images of the photographic subject obtained by the multiband imaging. However, data of a dental image may store: data on one normal captured image storing the value of RGB and the value of illuminance; and data on the seven spectral images of the photographic subject.

Next, the specular reflection region identification portion 13 detects positions of specular reflection regions in the tooth, the gum, and the background based on the data of the respective pixels constituting the dental image (step S2). A specular reflection region is a region in which light, such as illumination light, specularly reflects from a surface of a tooth or the like. However, a region brighter than certain brightness may be included in the concept of the specular reflection region although it is not specularly reflective. As will be described later in detail, if a value indicated by data of the respective pixels in the dental image exceeds a threshold value, a pixel relevant to the data is detected as a pixel within the specular reflection region.

The above threshold value may be fixedly set. However, in the case where signal values of the image data are increased or decreased as a whole, the above threshold value may be set based on the statistic values (average value and standard deviation) of the data of the respective pixels in the image. For example, in the case where outside light is incident on the dental image taking apparatus, there is a case where signal values of the image data are increased as a whole. If the threshold value is fixed in such a case, there is a case where a region which should not be extracted is erroneously recognized as a specular reflection region. On the other hand, in the case where a light amount of the illumination light is decreased over time, there is a case where signal values of the image data are decreased as a whole. Also in such a case, if the threshold value is fixed, there is a case where a region which should be extracted is not recognized as a specular reflection region. Therefore, by setting a threshold value based on the statistic values of the data of the respective pixels, the specular reflection region can be correctly recognized.

The specular reflection region identification portion 13 detects a position of a specular reflection region and generates a specular reflection map which shows a distribution of the specular reflection region in the dental image. In the present embodiment, of the seven bands (band 1: blue-violet, band 2: blue, band 3: light blue, band 4: blue-green, band 5: green, band 6: orange, band 7 red), the three bands of the band 1, the band 5, and the band 7 are selected to extract a specular reflection region. The band 1 is necessary for a coloring extraction, and some part of a specular reflection region can be extracted only with the band 1. The band 5 best clarifies a distinction between a tooth and a gum, allowing extraction of most of the specular reflection region on the tooth. The band 7 hardly distinguishes the tooth from the gum, and hence provides a good efficiency of wide-range specular reflection extraction on the gum.

The specular reflection region identification portion 13 extracts the data on the above three bands (band 1, band 5, and band 7) from the data on the seven bands in the dental images, divides the respective images into 8×8 pixel region, and calculates a standard deviation and average value of the pixel values in each region for the three bands, respectively. This is preliminary processing to make the processing speedy. Subsequently, as a wide-range specular reflection extraction, the specular reflection region identification portion 13 calculates a standard deviation and average value of the pixel values of the whole image for bands 1, 7, and then calculates a threshold value T1 for extracting a specular reflection region from these values. The specular reflection region identification portion 13 compares the pixel value with the threshold value T1 for every pixel, and extracts the pixel whose pixel value is above the threshold value T1 as a pixel within a specular reflection region, and to thereby identify this pixel as a pixel included in a specular reflection region.

As a specular reflection extraction on a small region, the specular reflection region identification portion 13 divides respective images into 64×64 pixel regions for the bands 1, 5, 7, calculates a standard deviation and average value of the pixel values for every region, and then calculates a threshold value T2 for every region from these values. The specular reflection region identification portion 13 uses the calculated threshold value T2 to extract a pixel within a specular reflection region in a 32×32 pixel region at the center of every region in a similar manner, to thereby identify this pixel as a pixel included in a specular reflection region.

As a dark colored portion extraction, the specular reflection region identification portion 13 extracts the data on bands 1, 5, 7, divides the respective images into 64×64 pixel regions, calculates a standard deviation and average value of the pixel values for every region, and then calculates a threshold value T3 for every region from these values. The specular reflection region identification portion 13 uses the calculated threshold value T3 to extract a pixel within a dark colored portion in a 32×32 pixel region at the center of every region in a similar manner, to thereby identify this pixel as a pixel included in a region of a dark colored portion. The specular reflection region identification portion 13 then generates a specular reflection map which stores data on the positions of the pixels extracted as pixels within a specular reflection region or a dark colored region (step S3).

Note that information which stores data on the positions of the pixels outside the specular reflection region or the darkly colored region may be used as a specular reflection map. Subsequently, the specular reflection region identification portion 13 transfers the specular reflection map to the rectangular range specification processing portion 12.

Figure 3:
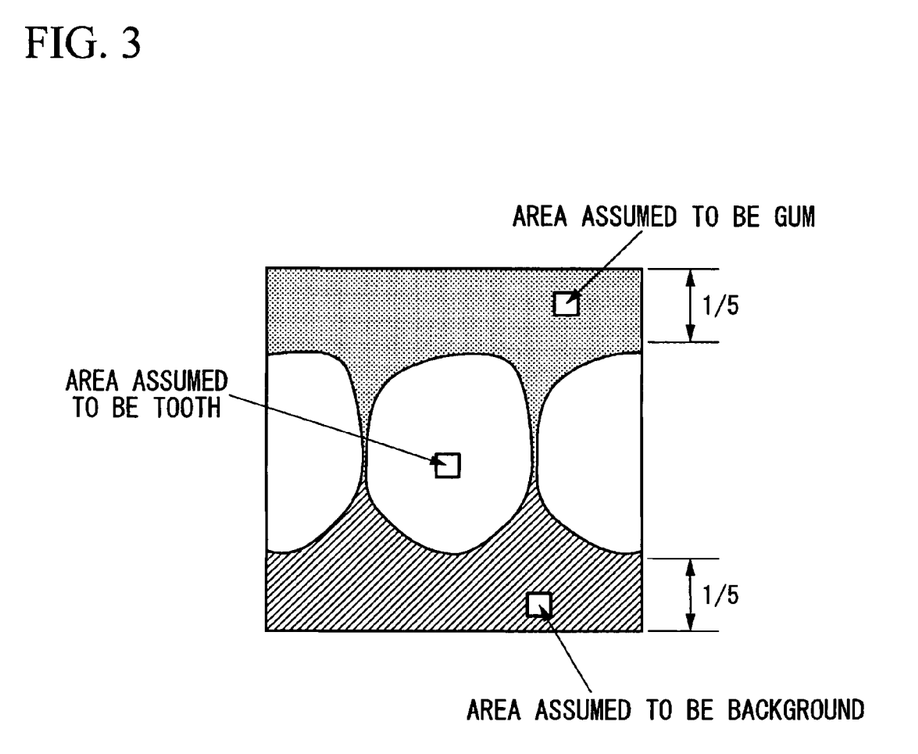
FIG. 3 is diagram for explaining an overview of a specifying method of rectangular ranges for initial recognition.

FIG. 3 is a diagram for explaining an overview of a specifying method of rectangular ranges for initial recognition.

On receiving the specular reflection map, the rectangular range specification processing portion 12 estimates a central portion of the dental image as a tooth, and moves a rectangular range including the pixels at the central portion in the left-right direction to specify a rectangular range not including a pixel which has been identified as a pixel showing a specular reflection in the specular reflection map, as a rectangular range for initial recognition in a tooth (step S4). Furthermore, the rectangular region specification processing portion 12 has already received input of information on whether the read dental image is a dental image on a maxillary area or a dental image on a mandibular area. According to the information, the rectangular region specification processing portion 12 specifies a rectangular range which is at a position in a predetermined range of the upper portion or lower portion of the dental image (for example, in the top ⅕ range of the image) and does not include a pixel identified as a pixel showing a specular reflection in the specular reflection map, as a rectangular range for initial recognition in a gum (step S5). Note that as a rectangular range for initial recognition in a gum, a range showing pixels which are determined as "heavy in red" based on the data on the dental image may be specified.

If the position estimated as the gum is in the upper portion of the dental image, the rectangular range specification processing portion 12 estimates a position in a predetermined range of the lower portion (for example, in the bottom ⅕ range of the image) as a background. If the position estimated as the gum is in the lower portion of the dental image, the rectangular range specification processing portion 12 estimates a position in a predetermined range of the upper portion (for example, in the top ⅕ range of the image) as a background. The rectangular range specification processing portion 12 further specifies a rectangular range including a pixel, of the pixels included in the background, which is not identified as a dark colored portion in the specular reflection map, as a rectangular range for initial recognition in a background (step S6). Note that a rectangular range for initial recognition in a background may be a range which is not a dark colored portion and shows pixels which are determined as "low in luminance." Here, a rectangular range for initial recognition specified respectively in a tooth, a gum, and a background is for example a rectangular range in a square shape with 12×12 pixels respectively in the vertical and horizontal directions. However, a rectangular range is not limited thereto. The rectangular range for initial recognition in each of a tooth, a gum, and a background is to be specified, to thereby determine a pixel with a color similar to that of the relevant rectangular range as a site identical to the site which the rectangular range for initial recognition is specified as. A detailed description of this processing will be given later.

After completion of the processing by the rectangular range specification processing portion 12, the site estimation processing portion 14 separately performs separation processing of the tooth from the gum (step S7) and separation processing of a dental incisal edge (a dental tip) from the background (step S8). In these processings, the rectangular range specification processing portion 12 uses the rectangular range for initial recognition in a part of a position estimated as a tooth and the rectangular range for initial recognition in a part of a position estimated as a gum to estimate a boundary between the tooth and the gum according to which of the tooth range and the gum range the pixels in the dental image other than the respective pixels within these rectangular ranges are positioned in (separation processing of the tooth from the gum). Furthermore, the site estimation processing portion 14 uses the rectangular range for initial recognition in a part of a position estimated as a tooth and the rectangular range for initial recognition in a part of a position estimated as a background to estimate a boundary between the tooth and the background according to which of the tooth range and the background range the pixels in the dental image other than the respective pixels within these rectangular ranges are positioned in (separation processing of the dental incisal edge from the background). In these processings, the site estimation processing portion 14 acquires a characteristic quantity (data on the seven bands) from the data of the pixels included in the rectangular ranges for initial recognition, and finds a classification vector which maximizes the Fisher ratio (=dispersion between two classes/dispersion within two classes). The site estimation processing portion 14 then compares an inner product between the classification vector and a pixel value vector with a threshold value to determine, for every pixel, which of the tooth and the gum a pixel is positioned in and which of the dental incisal edge and the background a pixel is positioned in.

In the separation processing in the site estimation processing portion 14, if the separation processing is separation processing of the tooth from the gum, information on band 1 of the pixels within the rectangular range for initial recognition in a tooth in the data of the dental image is read to be made as pixels of class 1, and information on band 1 of the pixels within the rectangular range for initial recognition in a gum in the data of the dental image is read to be made as pixels of class 2. If the separation processing is separation processing of the dental incisal edge from the background, information on band 1 of the pixels within the rectangular range for initial recognition in a tooth in the data of the dental image is read to be made as pixels of class 1, and information on band 1 of the pixels within the rectangular range for initial recognition in a background in the data of the dental image is read to be made as pixels of class 2.

Then, luminance components are extracted for every pixel in class 1 and class 2. Subsequently, an average value in luminance of band 1 of the pixels included in class 1 is detected. Here, the average value in luminance of band 1 of the pixels included in class 1 is made data da1, and the luminance of band 1 of the pixels in class 2 is made data db1.

Similarly, average values in luminance of band 2 to band 7 of the pixels included in class 1 are made da2 to da7, and average values in luminance of band 2 to band 7 of the pixels in class 2 are made db2 to db7. In this series of processings, the site estimation processing portion 14 writes data dai (where i=1 to 7) to luminance component memory A, and writes data dbi (where i=1 to 7) to luminance component memory B.

Furthermore, when taking a dental image, the site estimation processing portion 14 reads data of band 1 to band 7 from the image taking data of a reference plate R obtained by the dental image taking apparatus, and writes it to luminance component memory W as data dwi (i=1 to 7). Subsequently, the site estimation processing portion 14 reads data from the luminance component memory A and the luminance component memory W for class 1, and reads data from the luminance component memory B and the luminance component memory W for class 2, to thereby make a correction. In this correction, the data of the luminance component memory A is first divided by the data of the luminance component memory W for every filter component with the following formulae:

$$da^m i' = da^m i / dwi \text{ (where } i=1 \text{ to } 7, m=1 \text{ to } N) \qquad (1)$$

$$db^m i' = db^m i / dwi \text{ (where } i=1 \text{ to } 7, m=1 \text{ to } N) \qquad (2)$$

These calculations can eliminate influences of different light sources (vector characteristics). Here, i designates a filter number, and m designates a sample number. Furthermore, the site estimation processing portion 14 calculates the following formulae using power values $Ca^m$ and $Cb^m$ so as to make power values of the above divided data constant.

$$da^m i'' = da^m i' / Ca^m \text{ (where } i=1 \text{ to } 7, m=1 \text{ to } N) \qquad (3)$$

$$db^m i'' = db^m i' / Cb^m \text{ (where } i=1 \text{ to } 7, m=1 \text{ to } N) \qquad (4)$$

Here, the power values $Ca^m$ and $Cb^m$ are:

$$Ca^m = \sum_{i=1}^{N} da^m i' \qquad (5)$$

$$Cb^m = \sum_{i=1}^{N} db^m i'$$

or $$Ca^m = \sum_{i=1}^{N} (da^m i')^2 \qquad (6)$$

$$Cb^m = \sum_{i=1}^{N} (db^m i')^2$$

With these power normalizations, influences when luminance of the light source is different can be eliminated.

The site estimation processing portion 14 writes $da^m i''$ and $db^m i''$ thus found to luminance vector memory as luminance vectors. The above correction is repeated N times, which is the number of samples of two of the subjects (in the present embodiment, the tooth and the gum, or the dental incisal edge (dental tip) and the background).

Next, the site estimation processing portion 14 reads pieces of vector data respectively relating to class 1 and class 2 from the luminance vector memory, uses the FS (Foley Sammon) transform to find a classification vector d1i (where i=1 to 7) and a classification vector d2i (where i=1 to 7) which is orthogonal thereto, and writes them to classification vector memory respectively.

Next, the site estimation processing portion 14 reads the luminance vector data da$^m$i" from the luminance vector memory and reads the classification vector data d1$i$ from the classification vector memory, and then calculates an inner product as follows:

$$ta^m1 = \sum_{i=1}^{7}(da^mi'' \times d1i) \tag{7}$$

Furthermore, the site estimation processing portion 14 reads the luminance vector data db$^m$i" from the luminance vector memory and reads the classification vector data d1$i$ from the classification vector memory, and then calculates an inner product similarly as follows:

$$tb^m1 = \sum_{i=1}^{7}(da^mi'' \times d1i) \tag{8}$$

Furthermore, the site estimation processing portion 14 reads the luminance vector data da$^m$i" from the luminance vector memory and reads the classification vector data d2$i$ from the classification vector memory, and then calculates an inner product as follows:

$$ta^m2 = \sum_{i=1}^{7}(da^mi'' \times d2i) \tag{9}$$

Furthermore, the site estimation processing portion 14 reads the luminance vector data db$^m$i" from the luminance vector memory and reads the classification vector data d2$i$ from the classification vector memory, and then calculates an inner product as follows:

$$tb^m2 = \sum_{i=1}^{7}(db^mi'' \times d2i) \tag{10}$$

The site estimation processing portion 14 then writes the inner product values obtained by the formulae (7) to (10) to classification boundary memory.

Next, the site estimation processing portion 14 writes a luminance vector dxi (where i=1 to 7) to the luminance component memory in a similar manner to the above. Subsequently, the site estimation processing portion 14 writes a luminance vector dwi (where i=1 to 7) to the luminance component memory based on the information read from the image taking data of the reference plate R. Then, the site estimation processing portion 14 reads the data from this luminance component memory to calculate the following division:

dxi'=dxi/dwi (where i=1 to 7) (11)

Then, the site estimation processing portion 14 calculates the following formulae so that the power value of the divided data is normalized:

dxi″ = dxi′/Cx (where i = 1 to 7) (12)

$$Cx = \sum_{i=1}^{7} dxi'$$

and writes the luminance vector dxi" to the luminance vector memory. The site estimation processing portion 14 then reads the luminance vector dxi" from the luminance vector memory and reads the classification vector data d1$i$ from the classification vector memory, and then calculates an inner product as follows:

$$tx1 = \sum_{i=1}^{7}(dxi'' \times d1i) \tag{13}$$

Next, the site estimation processing portion 14 reads the luminance vector dxi" from the luminance vector memory and reads the classification vector data d2$i$ from the classification vector memory, and then calculates an inner product as follows:

$$tx2 = \sum_{i=1}^{7}(dxi'' \times d2i) \tag{14}$$

The site estimation processing portion 14 reads a classification boundary from the classification boundary memory. From this data, the site estimation processing portion 14 determines on which side of the classification boundary the above-calculated inner product values tx1, tx2 are, and outputs the classification results.

As described above, in the present embodiment, a characteristic quantity (data on the above seven bands) is obtained from the data of the pixels included in the rectangular ranges for initial recognition, and a classification vector which maximizes the Fisher ratio (=dispersion between two classes/dispersion within two classes) is found. The inner product between the found classification vector and the pixel value vector is compared with the threshold value to determine, for every pixel, which of the tooth and the gum a pixel is positioned in and which of the dental incisal edge and the background a pixel is positioned in. The difference in vector characteristic of the light source is corrected by division operations, and the difference in luminance is corrected by power normalization. Therefore, a favorable classification can be performed also for different light sources.

Then, the site estimation processing portion 14 performs the above separation processing in both of "the separation processing of the tooth from the gum" and "the separation processing of the dental incisal edge from the background", to thereby determine which of the tooth and the gum the respective pixels in the dental image are positioned in or which of the dental incisal edge and the background they are positioned in.

Figure 4:
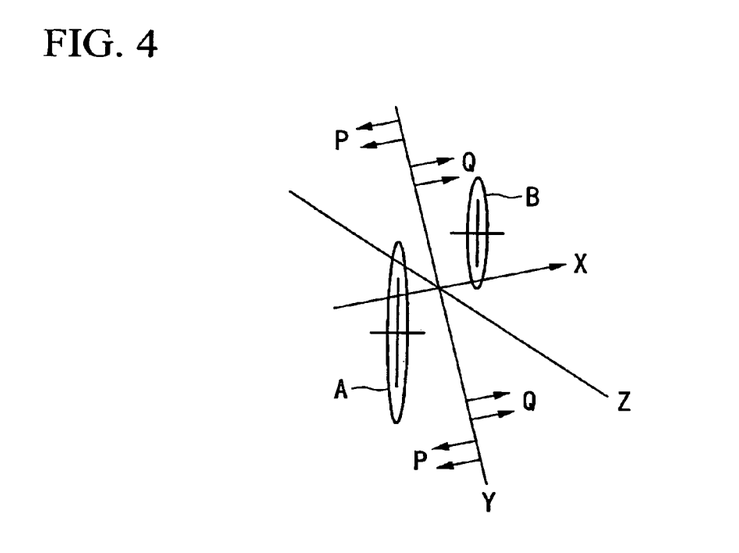
FIG. 4 shows an overview of separation processing.

FIG. 4 shows an overview of separation processing.

In FIG. 4, A denotes a set of class 1 (for example, pixels values on the tooth); B denotes a set of class 2 (for example, pixels values of the background); X denotes a classification vector; Y denotes a line of classification boundary by the threshold value and the classification vector; Z denotes a line of classification boundary by a perpendicular bisector of a line segment connecting the average coordinate of class 1 with the average coordinate of class 2; a region of P bounded by the classification boundary line of Y denotes a region determined as class 1; a region of Q bounded by the classification boundary line of Y denotes a region determined as class 2; and a black cross in A and B denotes an average value of pixels (a centroid). This figure shows a case where the pixel values of the classes are two dimensional. However, the values are seven dimensional because the number of bands is seven. In this figure, by a determination method using the classification boundary line of Z, a part of class 1 goes across the classification boundary line of Z, and the part is erroneously determined as class 2. However, use of the classification boundary line of Y (the present embodiment) can avoid an erroneous determination. Thus, in the dental image, color change by the way light is illuminated is significantly greater than color change inside the mouth such as the tooth (for example, specular reflection of light in the tooth or the like). When the pixels of the tooth and the pixels of the background are plotted on the coordinates of the seven bands, the regions of classes become ellipses in an extreme shape extending away from the original point. This makes image recognition by the conventional discrimination method using the classification boundary line of Z hardly possible. However, if the classification boundary line of Y is used as in the present invention, this problem can be solved.

Next, when estimating a boundary between a tooth and a gum in a dental image by use of the rectangular range in a part of the position estimated as the tooth and the rectangular range in a part of the position estimated as the gum, the site estimation processing portion 14 uses a new rectangular range, which is the rectangular range in a part of the position estimated as the tooth moved toward the gum, and a new rectangular range, which is the rectangular range in a part of the position estimated as the gum moved toward the tooth, to repeat processing for estimating a boundary between a tooth and a gum according to which of the tooth range and the gum range, the pixels in the dental image other than the respective pixels within the rectangular ranges are positioned in (processing similar to the above separation processing) (step S9). At this time, a plurality (two, in the present embodiment) of new rectangular ranges may be specified. Furthermore, the separation processing is repeated the same number of times as the new rectangular range, which is the rectangular range in a part of the position estimated as the tooth moved toward the gum, and the new rectangular range, which is the rectangular range in a part of the position estimated as the gum moved toward the tooth, are gradually brought closer to each other (twice, in the present embodiment).

Furthermore, when estimating a boundary between a tooth and a background in a dental image by use of the rectangular range in a part of the position estimated as the tooth and the rectangular range in a part of the position estimated as the background, the site estimation processing portion 14 uses a new rectangular range, which is the rectangular range in a part of the position estimated as the tooth moved toward the background, and a new rectangular range, which is the rectangular range in a part of the position estimated as the background moved toward the tooth, to repeat processing for estimating a boundary between a tooth and a background according to which of the tooth range and the background range, the pixels in the dental image other than the respective pixels within the rectangular ranges are positioned in (the above separation processing) (step S10). At this time, a plurality (two, in the present embodiment) of new rectangular ranges may be specified. Furthermore, the separation processing is repeated the same number of times as the new rectangular range, which is the rectangular range in a part of the position estimated as the tooth moved toward the background, and the new rectangular range, which is the rectangular range in a part of the position estimated as the background moved toward the tooth, are gradually brought closer to each other (twice, in the present embodiment).

Figure 5:
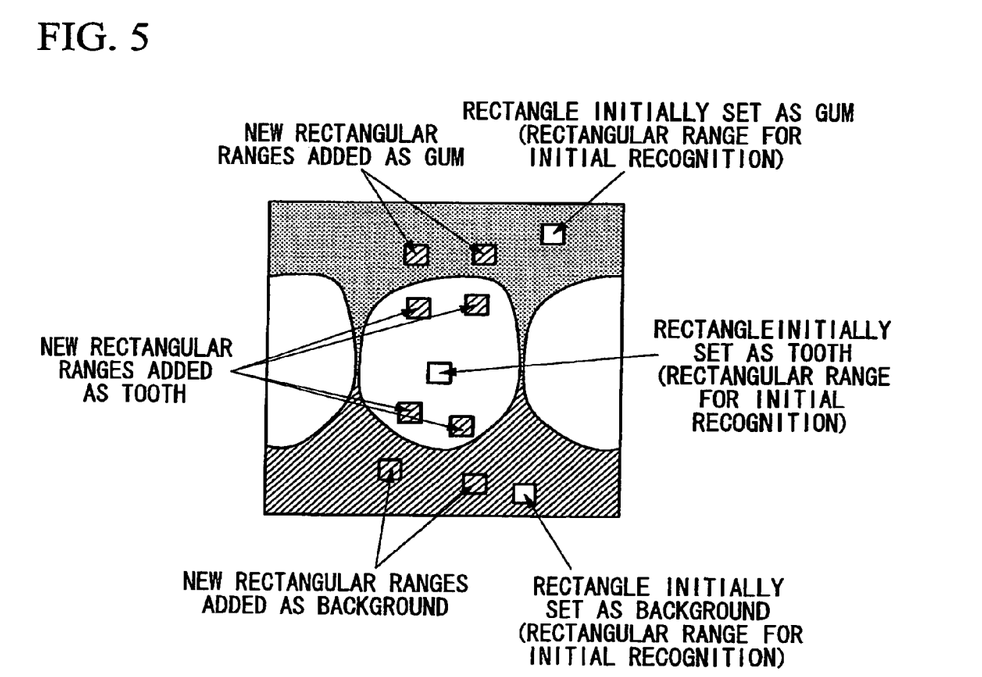
FIG. 5 is a first diagram showing an example of settings for new rectangular ranges.

FIG. 5 is a first diagram showing an example of settings for new rectangular ranges.

As shown in this figure, the site estimation processing portion 14 moves the rectangular range for initial recognition in a gum toward the tooth to specify two new rectangular ranges at different positions, and moves the rectangular range for initial recognition in a tooth toward the gum to specify two new rectangular ranges at different positions. As a result, the site estimation processing portion 14 performs separation processing for estimating a boundary between a tooth and a gum according to which of the tooth range and the gum range, pixels in the dental image other than the respective pixels in the rectangular ranges are positioned in. Similarly, the site estimation processing portion 14 moves the rectangular range for initial recognition in a background toward the tooth to specify two new rectangular ranges at different positions, and moves the rectangular range for initial recognition in a tooth toward the background (the incisal edge side) to specify two new rectangular ranges at different positions. As a result, the site estimation processing portion 14 performs separation processing for estimating a boundary between a tooth and a background according to which of the tooth range and the background range, pixels in the dental image other than the respective pixels in the rectangular ranges are positioned in.

Figure 6:
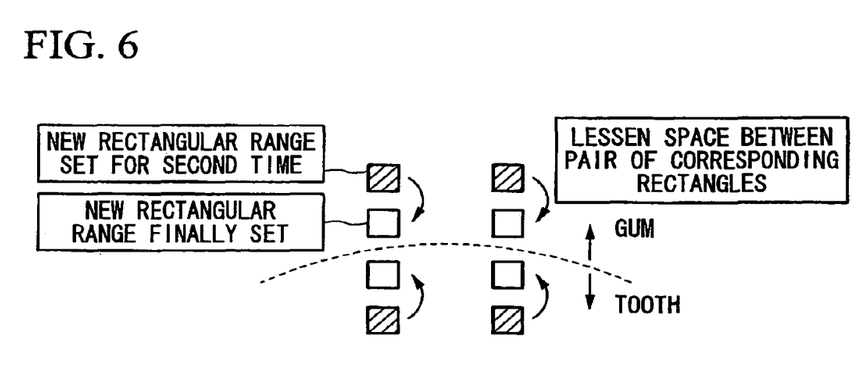
FIG. 6 is a second diagram showing an example of settings for new rectangular ranges.

FIG. 6 is a second diagram showing an example of settings for new rectangular ranges.

As shown in FIG. 6, the site estimation processing portion 14 performs separation processing the same number of times as the new rectangular range, which is the rectangular range in a part of the position estimated as the tooth moved toward the gum, and the new rectangular range, which is the rectangular range in a part of the position estimated as the gum moved toward the tooth, are gradually brought closer to each other (step S11). Similarly, the site estimation processing portion 14 performs separation processing the same number of times as the new rectangular range, which is the rectangular range in a part of the position estimated as the tooth moved toward the background, and the new rectangular range, which is the rectangular range in a part of the position estimated as the background moved toward the tooth, are gradually brought closer to each other (step S12). In the present embodiment, the specification of the new rectangular ranges is repeated twice to determine the final boundary. In the specification of the new rectangular ranges, the rectangular ranges may be moved from the original position by a set number of pixels. The site estimation processing portion 14 then stores in memory etc. information on which site of the tooth, the gum, and the background every pixel in the dental image is positioned in.

Figure 7:
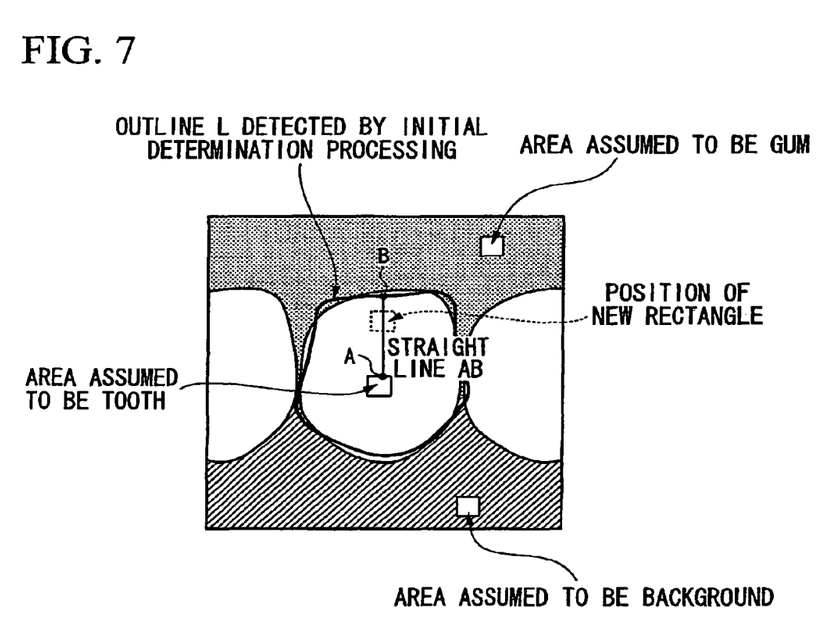
FIG. 7 is a third diagram showing an example of settings for new rectangular ranges.

FIG. 7 is a third diagram showing an example of settings for new rectangular ranges.

Note that the settings of the new rectangular ranges may be different from those in examples shown in FIG. 5 and FIG. 6.

For example, as shown in FIG. 7, in processing for separating the tooth from the gum, if the dental image is a dental image on the maxillary area, a position which internally divides a perpendicular line AB from the rectangle initially set as a tooth to an outline L detected by the first separation processing in step S7 or step S8 at a predetermined ratio (for example, 3:1) is set as a position for the new rectangular range. As a result, compared with the above example where a new rectangular range is gradually moved, the new rectangular range can be moved to the vicinity of an outline with less processing throughput. Therefore, the processing can be performed speedily. With a position setting of a new rectangular range by an internal division at an appropriate ratio, a position of a new rectangular range can be set without going beyond an outline detected by the first separation processing, even though the outline has an error. Therefore, processing can be performed without reducing the accuracy of the outline detection.

Figure 8:
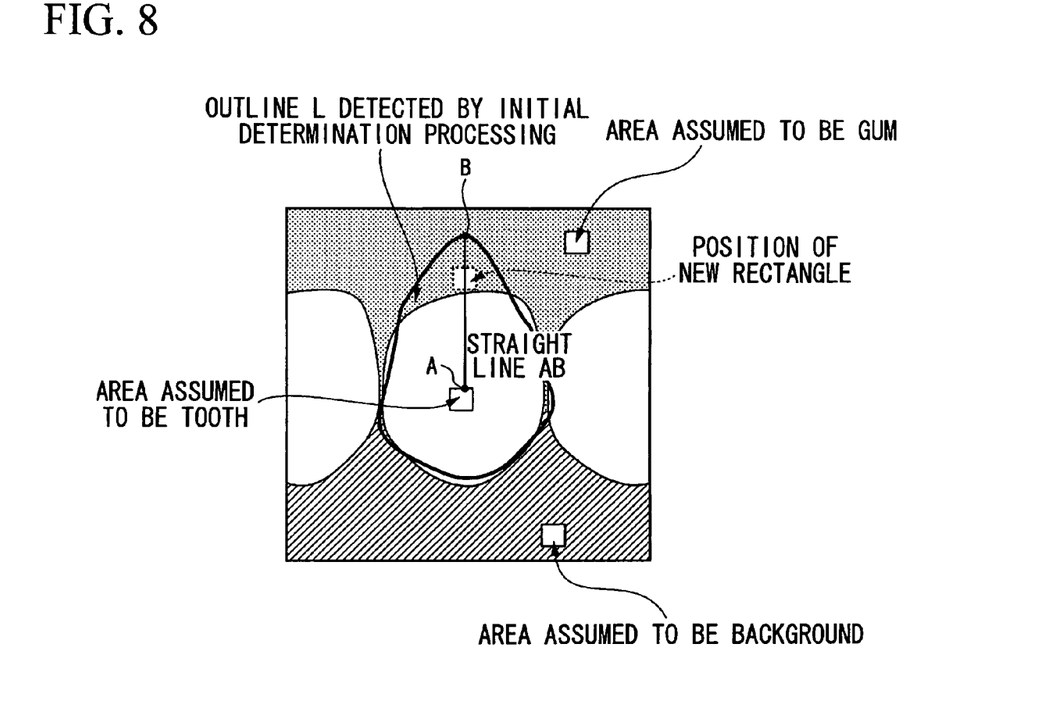
FIG. 8 is a fourth diagram showing an example of settings for new rectangular ranges.

FIG. 8 is a fourth diagram showing an example of settings for new rectangular ranges.

In the setting example of a new rectangular range described in FIG. 7, if a significant error has arisen between the outline L detected by the first processing in step S7 or step S8 and the actual outline as shown in FIG. 8, there is a possibility that the setting position of the new rectangular range goes into the gum region. To avoid such a setting of the new rectangular range, processing of determining whether the new rectangular range has gone into the gum region or not may be performed. Then, if the new rectangular range has gone into the gum region, processing of modifying the internal division ratio of the perpendicular line AB from the rectangle initially set as a tooth to the outline L may be performed.

In this case, the processing of determining whether the new rectangular range has gone into the gum region or not defines: an average signal of the pixels within the rectangular range initially set as a tooth, as $V1_{ave(i)}$ (i=1 to 7); an average signal of the pixels within the rectangular range initially set as a gum, as $V2_{ave(i)}$ (i=1 to 7); and an average signal of the pixels within the new rectangular range as $V3_{ave(i)}$ (i=1 to 7). Here, a tooth is close to white in color, and hence has a certain value or more of the respective wavelength components of the colors of the pixels within the rectangular range. Furthermore, the gum is close to red in color, and hence has a certain value or more of the red component $V2_{ave(7)}$ and has a small value of the blue component $V2_{ave(1)}$. Therefore, to compare ratios of band 1 to band 7, $P1=V1_{ave(1)}/V1_{ave(7)}$; $P2=V2_{ave(1)}/V2_{ave(7)}$; and $P3=V3_{ave(1)}/V3_{ave(7)}$ are defined.

If an operation value JG represented by $JG=|P3-P2|/|P1-P2|$ is large compared with the threshold value, the new rectangular range is determined to be at a correct tooth position. If the operation value JG is small compared with the threshold value, it is determined to be at the wrong gum position.

For example, if the operation value is 0.5 or greater, the new rectangular range is determined to be at the correct tooth position. If the operation value is less than 0.5, it is determined to be at a wrong gum position. Note that the operation value JG is a value which comes closer to 1 when the new rectangular range is positioned within the tooth, and comes closer to 0 when it is positioned within the gum. After the above determination processing, only when the new rectangular range is determined to be at a wrong position, the internal division ratio of the perpendicular line AB from the rectangle initially set as a tooth to the outline L is switched, and hence an outline can be detected with high speed and high accuracy.

Figure 9:
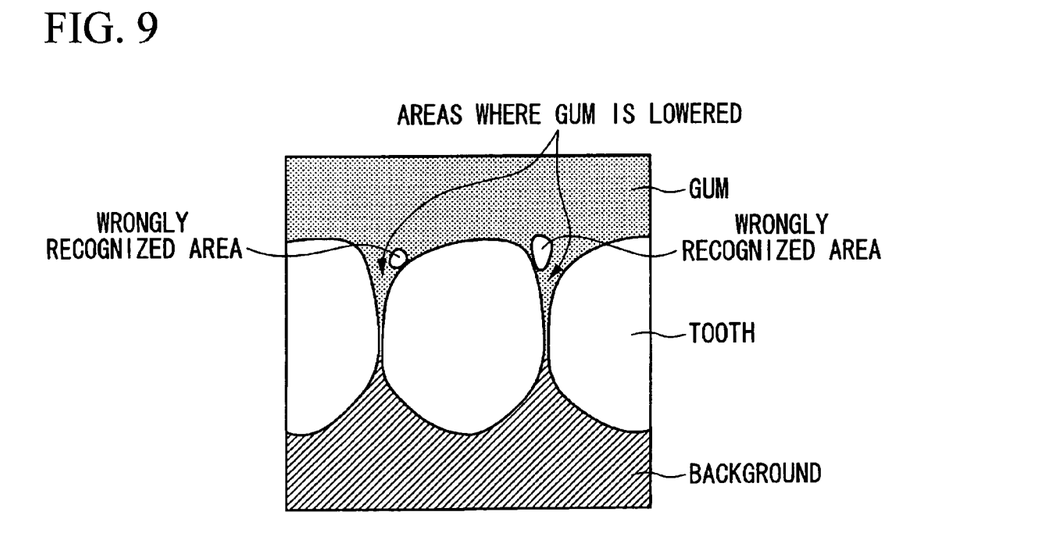
FIG. 9 shows an overview of processing by a mask processing portion.

After completion of the processing by the site estimation processing portion 14, the mask processing portion 15 performs mask processing (step S13). In the above processing by the site estimation processing portion 14, areas with smooth luminance change in the gum appear in the dental image on both sides of a tooth around which the gum has a tendency to be lowered. Therefore, there are cases where areas recognized as a tooth appear in a circular shape on a further gum side in vertical direction (on the upper side in the dental image of a maxillary area; on the lower side in the dental image of a mandibular area) than areas recognized as the gum on both sides of the tooth. This is obviously an erroneous recognition. Therefore, the mask processing portion 15 unconditionally determines a region further gum side in vertical direction than the rectangular range specified by the site estimation processing portion 14 as a site of the gum, as the gum. In the case where the region has been determined as a region of the tooth, it updates the information on the pixels thereof as a part of the gum. With this processing, erroneously recognized regions in a circular shape are eliminated (see FIG. 9, which shows an overview of processing by a mask processing portion.).

Figure 10:
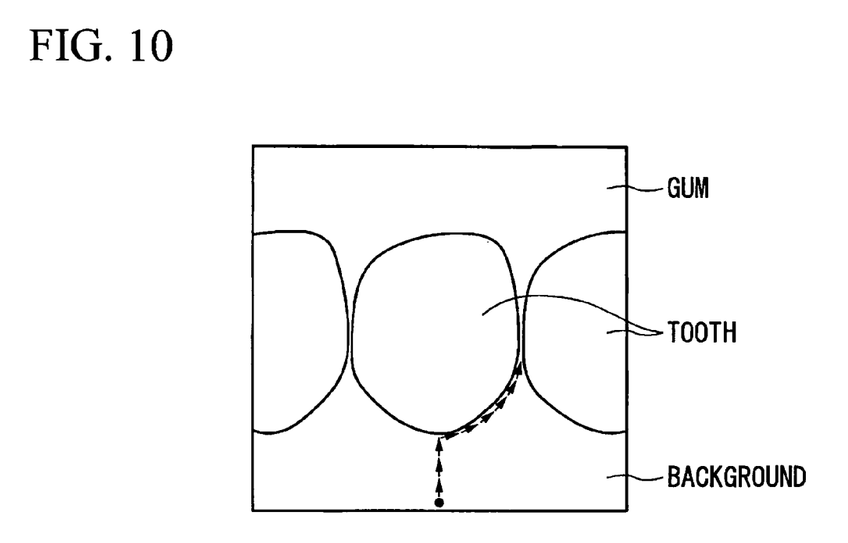
FIG. 10 shows an overview of processing by an outline calculation portion.

Next, the outline calculation portion 16 determines whether a pixel is estimated as in the range of the tooth one by one, starting at a pixel in the background near the incisal edge of the tooth toward the direction of the rectangular range specified as in the tooth range (the incisal edge side is suitable to start the determination of the outline because the incisal edge side has less noise). The outline calculation portion 16 identifies a boundary pixel one by one which is another pixel estimated as a tooth and is in contact with a pixel estimated as in another site (the background or the gum), starting counterclockwise at the pixel initially estimated as the tooth, and determines a set of the boundary pixels as an outline (step S14). Note that an edge of the dental image is unconditionally regarded as the background, to thereby reduce the number of conditional branches and make the processing speedy (see FIG. 10, which shows an overview of processing by an outline calculation portion.).

Here, the outline calculated by the processing of the outline calculation portion 16 is a line along the boundary line determined as the tooth by the region determination. However, the boundary of the set of colors determined as the tooth is jagged in many cases. Thus, since the outline is not a continuation of smooth lines, the smoothing processing portion 17 performs smoothing processing for correcting the outline into a smooth line (step S15). Furthermore, the outline calculated by the processing of the outline calculation portion 16 does not separate the adjacent teeth. Therefore, "distance between two points SQRT (Dx×Dx+Dy×Dy)" and "route length between two points Dindex" on the outline are all found. Then, as for all the two points on the outline, it is determined whether a ratio of "the route length between two points/the distance between two points" is larger than a predetermined threshold value or not. If the ratio is larger than the predetermined threshold value, the two points are directly connected and separation processing of adjacent teeth is performed. If it is smaller than the threshold value, separation processing of adjacent teeth is not performed. In this manner, two points are connected by a line, to thereby perform separation processing of adjacent teeth (step S16).

Figure 11:
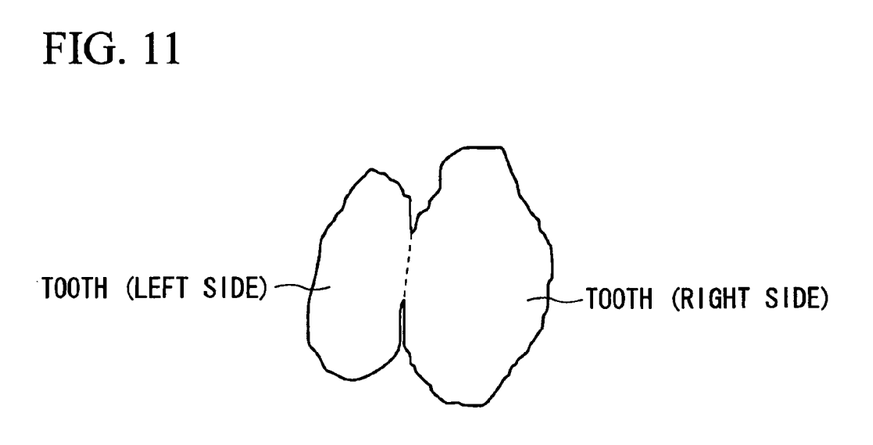
FIG. 11 shows an overview of separation processing of adjacent teeth.

FIG. 11 shows an overview of separation processing of adjacent teeth.

In this figure, a solid line represents an outline of teeth. A dashed line represents a separation line between the adjacent teeth. As for the route lengths along the outline from one point of both end points of the separation line to the other point, one along the outline of the tooth on the left side is shorter than one along the outline of the tooth on the right side. Furthermore, the length of the separation line between the adjacent teeth represented by the dashed line is much shorter than the route lengths along the outline from one point of both end points of the separation line to the other end point. In the example shown in FIG. 11, the route length along the outline from one point of both end points of the separation line to the other end point is four or more times as long as the length of the separation line between the adjacent teeth represented by the dashed line. Therefore, letting the threshold value between the length of the separation line between the adjacent teeth, and the route length along the outline from one point of both end points of the separation line to the other end point, be 4.0, the processing of separating the adjacent teeth is performed, and hence the separation line can be derived. The separation processing is repeated until the ratio of "the route length between two points/the distance between two points" fall below the threshold value, and the two points at which the ratio has fallen below the threshold value are connected, to thereby derive a separation line. Subsequently, the output portion 18 outputs the information after the processing by the smoothing processing portion 17, that is, the information on the outline calculated in the dental image, on for example a display screen to display an outline on the dental image in a superimposed manner.

An embodiment of the present invention has been described. According to the present invention, detection accuracy of an outline of a tooth in a dental image can be increased.

Note that the above outline detection apparatus has a computer system therewithin. The process of the above processings is stored in a recording medium readable by a computer, in a form of a program. The above processings are performed by a computer reading and executing this program. Here, a recording medium readable by a computer includes: a magnetic disk, a magneto optical disk, a CD-ROM, a DVD-ROM, and a semiconductor memory. This computer program may be distributed to a computer via a communication line, and the computer which has received this distribution may execute the program.

Furthermore, the above program may be one for actualizing a part of the above function.

Furthermore, it may be one which can actualize the above function by being combined with a program already stored in the computer system, that is, a difference file (a difference program).

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

According to the present invention, detection accuracy of an outline of a tooth in a dental image can be increased.

What is claimed is:

1. An outline detection apparatus which detects at least an outline of a tooth in a dental image of which are taken at least the tooth, a gum, and a background showing an inside of a mouth other than the tooth and the gum, comprising:
   a rectangular range specification device for estimating a central portion of the dental image as a tooth, estimating a position in a predetermined range in an upper or lower portion of the dental image as a gum according to a specification of a dental image on a maxillary area or a mandibular area, estimating a position in a predetermined range in the lower portion as the background if the position estimated as the gum is in the upper portion of the dental image, or estimating a position in a predetermined range in the upper portion as the background if the position estimated as the gum is in the lower portion of the dental image, and specifying rectangular ranges with predetermined pixels in a part of the positions estimated as the tooth, the gum, and the background; and
   a site estimation device for acquiring from data on the dental image a characteristic quantity based on color information of the respective pixels in the rectangular ranges, finding a classification vector which maximizes the Fischer ratio based on the acquired characteristic quantity, and estimating which of the tooth range, the gum range, and the background range, pixels in the dental image other than the respective pixels in the rectangular ranges are positioned in according to comparison between a predetermined threshold value and an inner product between the classification vector and a pixel value vector based on color information on pixels in the dental image other than the respective pixels in the rectangular ranges.

2. The outline detection apparatus according to claim 1, wherein the site estimation device separately performs:
   processing in which the rectangular range in a part of the position estimated as the tooth and the rectangular range in a part of the position estimated as the gum are used to estimate a boundary between a tooth and a gum according to which of the tooth range and the gum range, the pixels in the dental image other than the respective pixels within the rectangular ranges are positioned in; and
   processing in which the rectangular range in a part of the position estimated as the tooth and the rectangular range in a part of the position estimated as the background are used to estimate a boundary between a tooth and a background according to which of the tooth range and the background range, the pixels in the dental image other than the respective pixels within the rectangular ranges are positioned in.

3. The outline detection apparatus according to claim 2, wherein
   when estimating a boundary between a tooth and a gum by use of the rectangular range in a part of the position estimated as the tooth and the rectangular range in a part of the position estimated as the gum, the site estimation device uses a new rectangular range, which is the rectangular range in a part of the position estimated as the tooth moved toward the gum, and a new rectangular range, which is the rectangular range in a part of the position estimated as the gum moved toward the tooth, to repeat processing for estimating a boundary between a tooth and a gum according to which of the tooth range and the gum range, the pixels in the dental image other than the respective pixels within the rectangular ranges are positioned in,
   the processing being repeated the same number of times as the new rectangular range, which is the rectangular range in a part of the position estimated as the tooth moved toward the gum, and the new rectangular range, which is the rectangular range in a part of the position estimated as the gum moved toward the tooth, are gradually brought closer to each other.

4. The outline detection apparatus according to claim 2, wherein
   when estimating a boundary between a tooth and a background by use of the rectangular range in a part of the position estimated as the tooth and the rectangular range in a part of the position estimated as the background, the site estimation device uses a new rectangular range, which is the rectangular range in a part of the position estimated as the tooth moved toward the background, and a new rectangular range, which is the rectangular range in a part of the position estimated as the background moved toward the tooth, to repeat processing for estimating a boundary between a tooth and a background according to which of the tooth range and the background range, the pixels in the dental image other than the respective pixels within the rectangular ranges are positioned in,
   the processing being repeated the same number of times as the new rectangular range, which is the rectangular range in a part of the position estimated as the tooth moved toward the background, and the new rectangular range, which is the rectangular range in a part of the position estimated as the background moved toward the tooth, are gradually brought closer to each other.

5. The outline detection apparatus according to claim 2, further comprising:
an outline calculation portion which determines whether or not a pixel is the pixel estimated as in the tooth range one by one from the pixel in the vicinity of the tooth toward the rectangular range in a part of the position estimated as the tooth, and then identifies, one by one from a pixel initially estimated as in the tooth range, a boundary pixel that is another pixel estimated as in the tooth range and is in contact with the pixel estimated as in a site other than the tooth, to thereby determine a set of the boundary pixels as an outline.

6. The outline detection apparatus according to claim 1, wherein the site estimation device specifies the rectangular range in a part of the position estimated as the tooth outside a region of the tooth in which light is specularly reflected.

7. An outline detection method which detects at least an outline of a tooth in a dental image of which are taken at least the tooth, a gum, and a background showing an inside of a mouth other than the tooth and the gum, comprising:
a rectangular range specification process for estimating a central portion of the dental image as a tooth, estimating a position in a predetermined range in an upper or lower portion of the dental image as a gum according to a specification of a dental image on a maxillary area or a mandibular area, estimating a position in a predetermined range in the lower portion as the background if the position estimated as the gum is in the upper portion of the dental image, or estimating a position in a predetermined range in the upper portion as the background if the position estimated as the gum is in the lower portion of the dental image, and specifying rectangular ranges with predetermined pixels in a part of the positions estimated as the tooth, the gum, and the background; and
a site estimation process for acquiring from data on the dental image a characteristic quantity based on color information of the respective pixels in the rectangular ranges, finding a classification vector which maximizes the Fischer ratio based on the acquired characteristic quantity, and estimating which of the tooth range, the gum range, and the background range, pixels in the dental image other than the respective pixels in the rectangular ranges are positioned in according to comparison between a predetermined threshold value and an inner product between the classification vector and a pixel value vector based on color information on pixels in the dental image other than the respective pixels in the rectangular ranges.

8. The outline detection method according to claim 7, wherein the site estimation process includes a process for separately performing:
processing in which the rectangular range in a part of the position estimated as the tooth and the rectangular range in a part of the position estimated as the gum are used to estimate a boundary between a tooth and a gum according to which of the tooth range and the gum range, the pixels in the dental image other than the respective pixels within the rectangular ranges are positioned in; and
processing in which the rectangular range in a part of the position estimated as the tooth and the rectangular range in a part of the position estimated as the background are used to estimate a boundary between a tooth and a background according to which of the tooth range and the background range, the pixels in the dental image other than the respective pixels within the rectangular ranges are positioned in.

9. The outline detection method according to claim 8, wherein
the site estimation process comprises a process in which when estimating a boundary between a tooth and a gum by use of the rectangular range in a part of the position estimated as the tooth and the rectangular range in a part of the position estimated as the gum, the site estimation process uses a new rectangular range, which is the rectangular range in a part of the position estimated as the tooth moved toward the gum, and a new rectangular range, which is the rectangular range in a part of the position estimated as the gum moved toward the tooth, to repeat processing for estimating a boundary between a tooth and a gum according to which of the tooth range and the gum range, the pixels in the dental image other than the respective pixels within the rectangular ranges are positioned in,
the processing being repeated the same number of times as the new rectangular range, which is the rectangular range in a part of the position estimated as the tooth moved toward the gum, and the new rectangular range, which is the rectangular range in a part of the position estimated as the gum moved toward the tooth, are gradually brought closer to each other.

10. The outline detection method according to claim 8, wherein
the site estimation process comprises a process in which when estimating a boundary between a tooth and a background by use of the rectangular range in a part of the position estimated as the tooth and the rectangular range in a part of the position estimated as the background, the site estimation process uses a new rectangular range, which is the rectangular range in a part of the position estimated as the tooth moved toward the background, and a new rectangular range, which is the rectangular range in a part of the position estimated as the background moved toward the tooth, to repeat processing for estimating a boundary between a tooth and a background according to which of the tooth range and the background range, the pixels in the dental image other than the respective pixels within the rectangular ranges are positioned in,
the processing being repeated the same number of times as the new rectangular range, which is the rectangular range in a part of the position estimated as the tooth moved toward the background, and the new rectangular range, which is the rectangular range in a part of the position estimated as the background moved toward the tooth, are gradually brought closer to each other.

11. The outline detection method according to claim 8, further comprising:
an outline calculation process which determines whether or not a pixel is the pixel estimated as in the tooth range one by one from the pixel in the vicinity of the tooth toward the rectangular range in a part of the position estimated as the tooth, and then identifies, one by one from a pixel initially estimated as in the tooth range, a boundary pixel that is another pixel estimated as in the tooth range and is in contact with the pixel estimated as in a site other than the tooth, to thereby determine a set of the boundary pixels as an outline.

12. The outline detection method according to claim 7, further comprising
 a process for specifying the rectangular range in a part of the position estimated as the tooth outside a region of the tooth in which light is specularly reflected.

13. A non-transitory computer-readable medium having a program stored thereon for controlling a computer of an outline detection apparatus which detects at least an outline of a tooth in a dental image of which are taken at least the tooth, a gum, and a background showing an inside of a mouth other than the tooth and the gum to execute:
 rectangular range specification processing for estimating a central portion of the dental image as a tooth, estimating a position in a predetermined range in an upper or lower portion of the dental image as a gum according to a specification of a dental image on a maxillary area or a mandibular area, estimating a position in a predetermined range in the lower portion as the background if the position estimated as the gum is in the upper portion of the dental image, or estimating a position in a predetermined range in the upper portion as the background if the position estimated as the gum is in the lower portion of the dental image, and specifying rectangular ranges with predetermined pixels in a part of the positions estimated respectively as the tooth, the gum, and the background; and
 site estimation processing for acquiring from data on the dental image a characteristic quantity based on color information of the respective pixels in the rectangular ranges, finding a classification vector which maximizes the Fischer ratio based on the acquired characteristic quantity, and estimating which of the tooth range, the gum range, and the background range, pixels in the dental image other than the respective pixels in the rectangular ranges are positioned in according to comparison between a predetermined threshold value and an inner product between the classification vector and a pixel value vector based on color information on pixels in the dental image other than the respective pixels in the rectangular ranges.

14. The outline detection apparatus according to claim 3, wherein the site estimation device specifies the rectangular range or the new rectangular range in a part of the position estimated as the tooth outside a region of the tooth in which light is specularly reflected.

15. The outline detection apparatus according to claim 4, wherein the site estimation device specifies the rectangular range or the new rectangular range in a part of the position estimated as the tooth outside a region of the tooth in which light is specularly reflected.

16. The outline detection method according to claim 9, further comprising:
 a process for specifying the rectangular range or the new rectangular range in a part of the position estimated as the tooth outside a region of the tooth in which light is specularly reflected.

17. The outline detection method according to claim 10, further comprising:
 a process for specifying the rectangular range or the new rectangular range in a part of the position estimated as the tooth outside a region of the tooth in which light is specularly reflected.

* * * * *